(12) United States Patent
Kompella et al.

(10) Patent No.: US 9,440,959 B2
(45) Date of Patent: *Sep. 13, 2016

(54) PROCESS FOR THE PREPARATION OF NILOTINIB

(71) Applicant: Natco Pharma Limited, Banjara Hills (IN)

(72) Inventors: Amala Kompella, Banjara Hills (IN); Adibhatla Kali Satya Bhujanga Rao, Banjara Hills (IN); Sreenivas Rachakonda, Banjara Hills (IN); Venugopala Krishna Gampa, Banjara Hills (IN); Venkaiah Chowdary Nannapaneni, Banjara Hills (IN)

(73) Assignee: Natco Pharma Limited, Banjara Hills, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/660,628

(22) Filed: Mar. 17, 2015

(65) Prior Publication Data

US 2015/0183762 A1  Jul. 2, 2015

Related U.S. Application Data

(63) Continuation of application No. 13/397,640, filed on Feb. 15, 2012, now Pat. No. 9,061,028.

(51) Int. Cl.
C07D 401/14 (2006.01)
A61K 31/506 (2006.01)
C07D 233/61 (2006.01)

(52) U.S. Cl.
CPC ........... *C07D 401/14* (2013.01); *A61K 31/506* (2013.01); *C07D 233/61* (2013.01); *C07B 2200/13* (2013.01)

(58) Field of Classification Search
CPC .................... C07D 401/14; A61K 31/506
USPC .......................................... 544/331; 514/275
See application file for complete search history.

(56) References Cited

U.S. PATENT DOCUMENTS

| 7,169,791 | B2 | 1/2007 | Breitenstein et al. |
| 7,910,598 | B2 | 3/2011 | Kompella et al. |
| 8,426,404 | B2 | 4/2013 | Zhang et al. |
| 9,061,028 | B2* | 6/2015 | Kompella ............ C07D 401/14 |
| 2006/0149061 | A1 | 7/2006 | Anli et al. |
| 2008/0269269 | A1 | 10/2008 | Manley et al. |

FOREIGN PATENT DOCUMENTS

| IN | 768/CHE/2010 | 9/2011 |
| WO | 2004/005281 A1 | 1/2004 |
| WO | 2007/015870 A2 | 2/2007 |
| WO | 2007/092531 A2 | 8/2007 |
| WO | 2009/109991 A2 | 9/2009 |

(Continued)

OTHER PUBLICATIONS

Liu, Rong, ed., Water-Insoluble Drug Formulation (CRC Press, 2008), Chapter 15, pp. 417-435.*
Huang et al., "An Efficient Synthesis of Nilotinib (AMN107)," Synthesis (2007) 14: 2121-2124.

(Continued)

*Primary Examiner* — Deepak Rao
(74) *Attorney, Agent, or Firm* — Mintz, Levin, Cohn, Ferris, Glovsky and Popeo, P.C.

(57) ABSTRACT

The present invention relates a process for the preparation of a compound of formula (I):

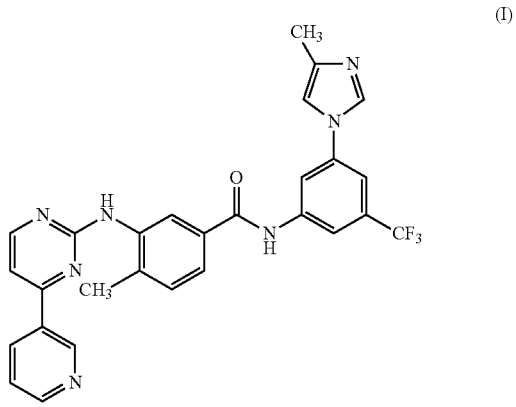

or a pharmaceutically acceptable salt thereof,
which process comprises converting a compound of formula (IV):

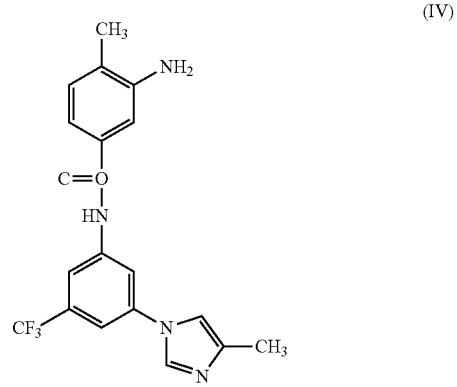

or a pharmaceutically acceptable salt thereof, into the compound of formula (I) or a pharmaceutically acceptable salt thereof.

4 Claims, 2 Drawing Sheets

(56) References Cited

FOREIGN PATENT DOCUMENTS

| WO | 2010/054056 A2 | 5/2010 |
| WO | 2010/060074 A1 | 5/2010 |
| WO | 2011/033307 A1 | 3/2011 |
| WO | WO 2011/086541 A1 * | 7/2011 |
| WO | 2011/163222 A1 | 12/2011 |

OTHER PUBLICATIONS

Seeliger et al., "Equally Potent Inhibition of c-Src and Abl by Compounds that recognize inactive kinase confirmatinos," *Cancer Research* (2009) 69(6):2384-2392.

Bursavich et al., "Expedient Parallel Synthesis of 2-Amino-4-heteroarylpyrimidines," *Organic Letters* (2005) 7(19):4113-4116.

* cited by examiner

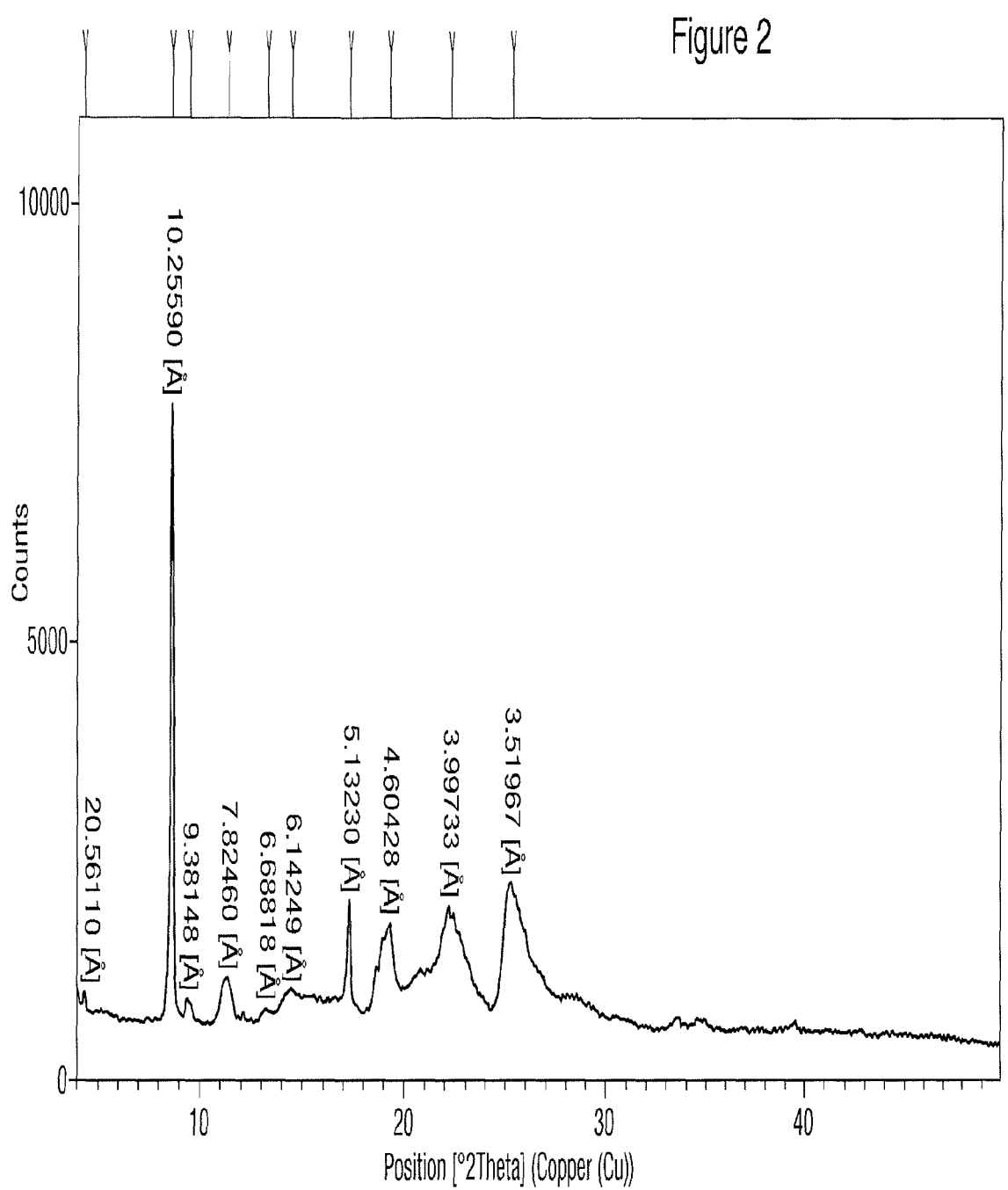

PROCESS FOR THE PREPARATION OF NILOTINIB

FIELD OF THE INVENTION

The present invention is concerned with a process for the preparation of Nilotinib and Nilotinib hydrochloride.

BACKGROUND OF THE INVENTION

Nilotinib is the compound 4-methyl-N[3-(4-methyl-1H-imidazol-1-yl-5-(trifluoromethyl)phenyl]-3-{{4-(3-pyridinyl)-2-pyrimidinyl]amino]benzamide and is of Formula (I):

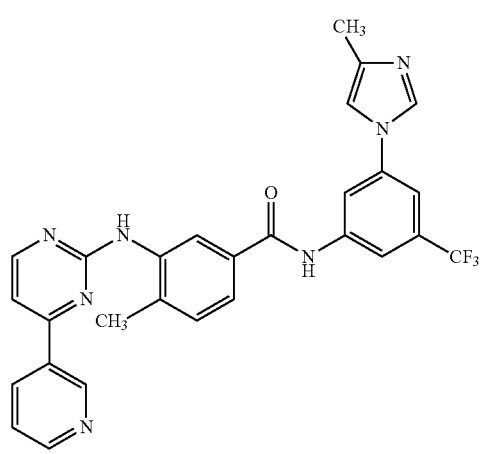

(I)

Nilotinib is a protein tyrosine kinase inhibitor.

The preparation of Nilotinib and the use thereof, especially as an antitumor agent, are described in WO 2004/005281 (Novartis Pharma) which was published on 15 Jan. 2004. WO 2004/005281 (which corresponds to U.S. Pat. No. 7,169,791) describes the synthetic route depicted in Scheme 1 below.

SCHEME 1

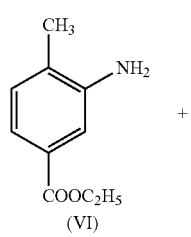

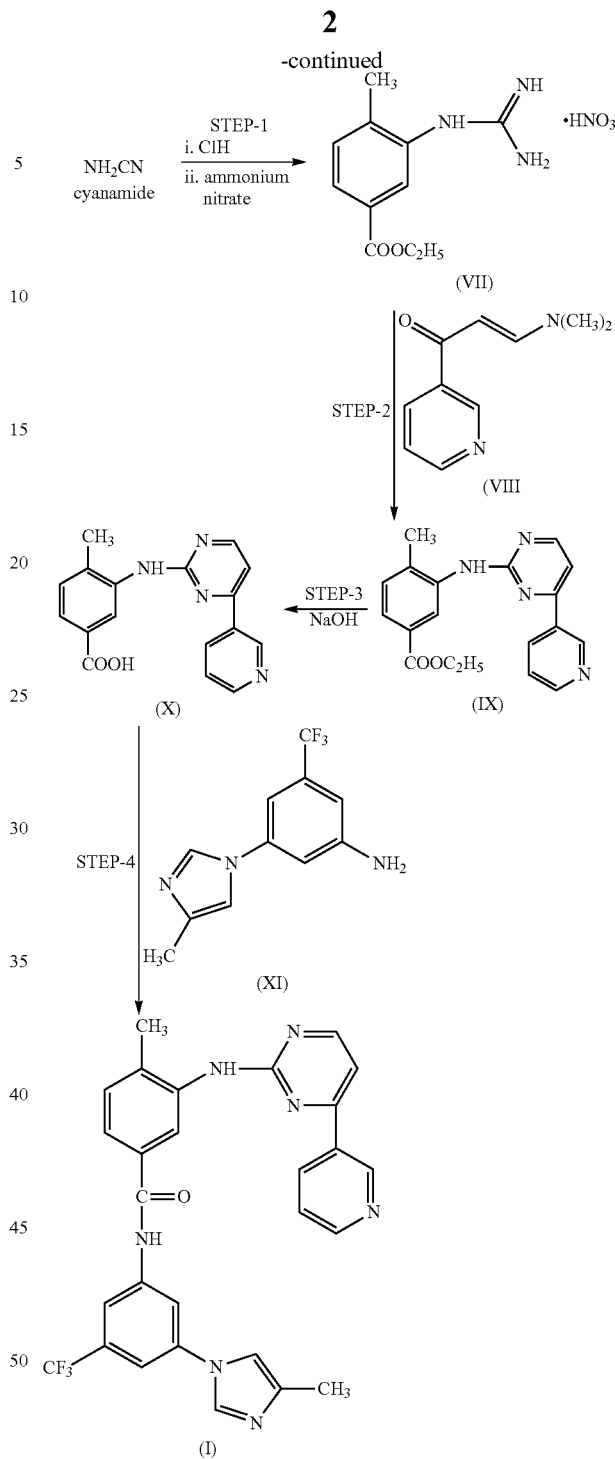

The specific reagents and reaction conditions used in this process are described in WO 2004/005281. The present inventors have observed the following problems with the process described in WO 2004/005281:

1. In step-1
   (i) The yield of compound of formula (VII) is very low (25-30%) with low purity (90%).
2. In step-2
   (i). The yield of compound of formula (IX) is low (35%) making the process unviable.
   (ii) The reaction time is very lengthy (65 hours), which could be problematic for commercial scale operations.

(iii) Use of diethyl ether is not adaptable on commercial scale production because it is highly flammable and very volatile.

3. In step-4
   (i) The yield of compound of formula (I) is very low (20-30%) thereby making the process uneconomical for commercial production.
   (ii) Usage of the toxic and expensive propyl phosphonic anhydride as a reagent makes this process impractical for manufacturing scale operations.

There therefore exists a need for an improved process for manufacturing Nilotinib, which achieves high yields and purity, combined with overall process efficiency.

SUMMARY OF THE INVENTION

The present inventors have devised a new process for preparing Nilotinib and its pharmaceutically acceptable salts. The process is more efficient than prior art processes, with high yields in each step (60-97%) as compared to the prior art processes (20-50%) in WO 2004/005281 discussed above. Further, reaction times in the process of the invention are low (9-20 hours) at each step as compared to the reaction times (12-65 hours) for many of the steps in the prior art process.

In addition, the process of the present invention avoids the use of obnoxious, foul smelling and difficult to handle reagents, which makes the process environmentally safe for commercial application. In summary, the process of the present invention is efficient, economical and viable for plant scale operations.

Furthermore, the present inventors have surprisingly found that the final product (Nilotinib or a pharmaceutically acceptable salt thereof) of the process of the present invention exists in a stable crystal form. This form is retained, even under accelerated stress conditions (for example an elevated temperature of 40° C. combined with relative humidity of 75%). It is particularly surprising that the present process allows preparation of a stable form of Nilotinib hydrochloride dihydrate, which was previously believed to be unstable.

Accordingly, the present invention relates to a process for the preparation of a compound of formula (I):

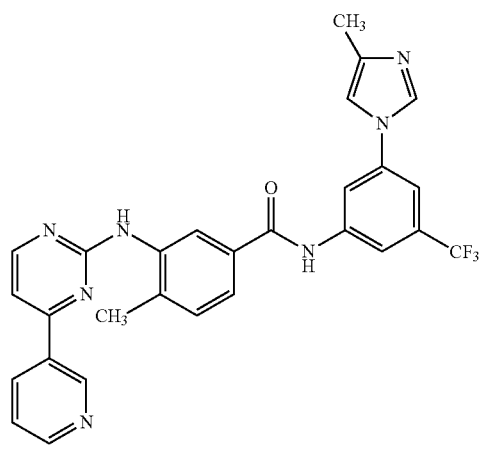

or a pharmaceutically acceptable salt thereof,
which process comprises converting a compound of formula (IV):

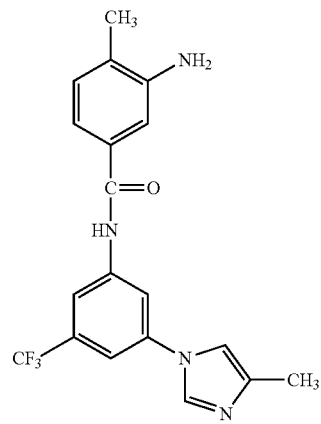

or a pharmaceutically acceptable salt thereof, into the compound of formula (I) or a pharmaceutically acceptable salt thereof.

The invention further relates to a compound of formula (IV):

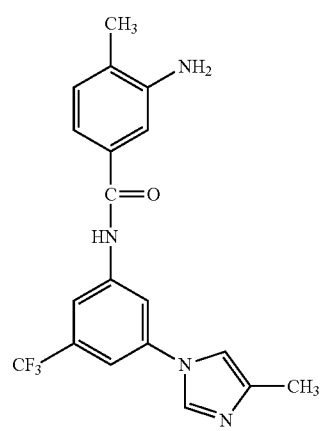

or a pharmaceutically acceptable salt thereof.

The invention further provides a compound of formula (V):

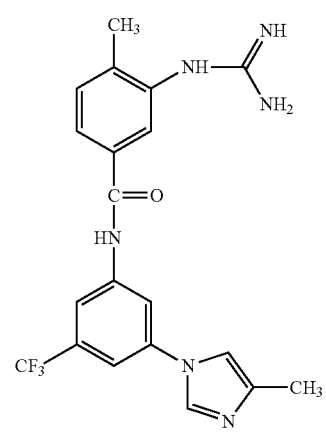

or a pharmaceutically acceptable salt thereof.

The invention also relates to a process for preparing a compound of formula (IV), or a pharmaceutically acceptable salt thereof, which process comprises reducing the nitro moiety of a compound of formula (III)

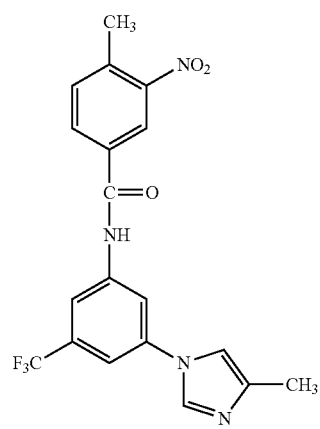
(III)

or a pharmaceutically acceptable salt thereof.

The invention also provides a process for preparing a compound of formula (V), or a pharmaceutically acceptable salt thereof, which process comprises reacting a compound of formula (IV), or a pharmaceutically acceptable salt thereof, with cyanamide to obtain a compound of formula (V) or a pharmaceutically acceptable salt thereof.

The invention further provides a compound of formula

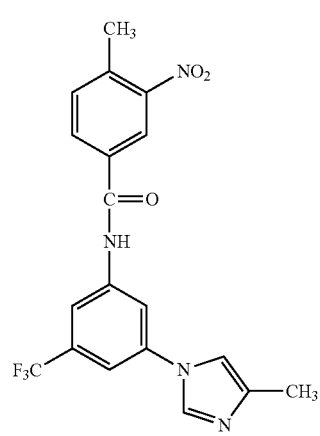
(III)

or a pharmaceutically acceptable salt thereof.

The invention also relates to a process for preparing a compound of formula (III), or a pharmaceutically acceptable salt thereof, which process comprises reacting a compound of formula (XI):

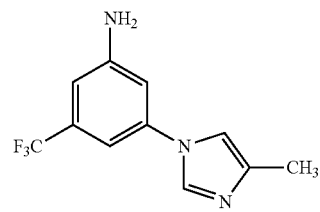
(XI)

or a pharmaceutically acceptable salt thereof, with a compound of formula (IIA):

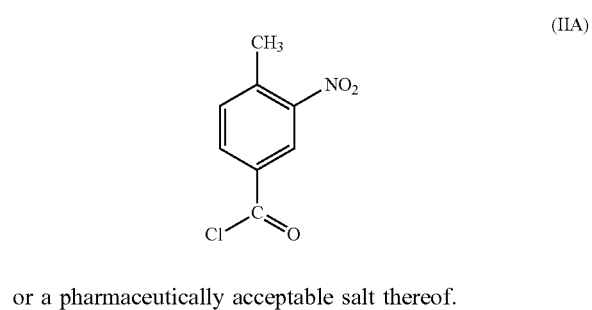
(IIA)

or a pharmaceutically acceptable salt thereof.

The invention is also directed to a compound of formula (I) or a pharmaceutically acceptable salt thereof obtainable by the process of the invention.

The invention further provides a crystalline form of a compound of formula (I):

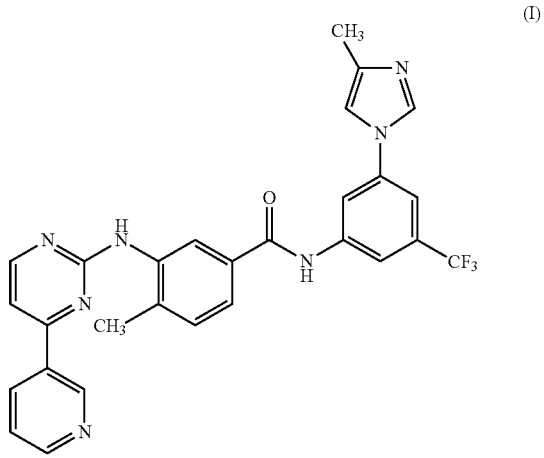 [SMILES: Cc1cn(-c2cc(NC(=O)c3ccc(C)c(Nc4nccc(-c5cccnc5)n4)c3)cc(C(F)(F)F)c2)cn1]
(I)

or a pharmaceutically acceptable salt thereof, which has an X-ray powder diffraction pattern with one or more peaks at 4.3, 8.7, 9.5, 11.3, 13.2, 14.4, 17.3, 18.6, 19.3, 20.8, 22.2 and 25.3 degrees 2θ (±0.1 degrees 2θ).

The invention is also directed to a pharmaceutical composition comprising a compound of formula (I) or a pharmaceutically acceptable salt thereof obtainable by the process of the invention or a crystalline form of the invention in association with a pharmaceutically acceptable diluent or carrier.

BRIEF DESCRIPTION OF THE FIGURES

FIG. 2 shows the X-ray powder diffraction pattern for the Nilotinib hydrochloride formulation prepared in Example 3.

DETAILED DESCRIPTION OF THE INVENTION

Figure 1:
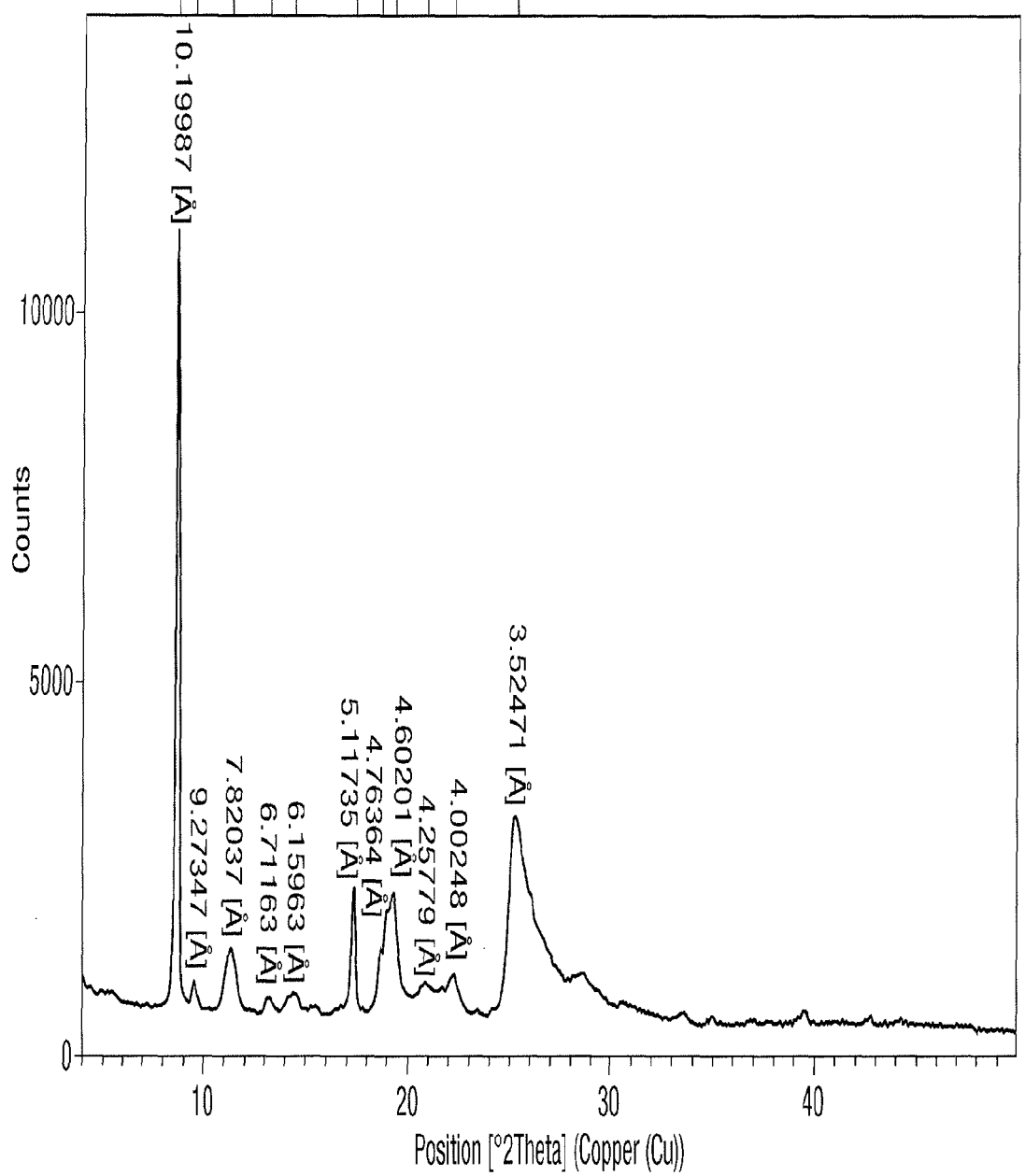
FIG. 1 shows the X-ray powder diffraction pattern for the Nilotinib hydrochloride prepared in Example 1(e).

The term "pharmaceutically acceptable salt" typically refers to a salt prepared from an acid which is acceptable for administration to a patient, such as a mammal. Such salts can be derived from from pharmaceutically acceptable inorganic or organic acids.

Salts derived from pharmaceutically acceptable acids include acetic, benzenesulfonic, benzoic, camphosulfonic, citric, ethanesulfonic, formic, fumaric, gluconic, glutamic, hydrobromic, hydrochloric, hydrofluoric, lactic, maleic, malic, mandelic, methanesulfonic, trifluoroacetic, mucic, nitric, pantothenic, phosphoric, succinic, sulfuric, tartaric, p toluenesulfonic, xinafoic (1 hydroxy 2 naphthoic acid), napadisilic (1,5 naphthalenedisulfonic acid), triphenyl acetic and the like. Particularly preferred are salts derived from formic, fumaric, hydrobromic, hydrochloric, hydrofluoric, acetic, sulfuric, methanesulfonic, trifluoroacetic, xinafoic, tartaric, maleic, succinic and napadisilic acids. A particularly preferred pharmaceutically acceptable salt is hydrochloride.

An illustrative example of an overall process of the present invention is depicted in Scheme 2 below. As a skilled person will appreciate, each of intermediate compounds (II), (IIA), (XI), (III), (IV), (V) and (VI) may be used in free base form or in the form of a pharmaceutically acceptable salt. Generally the free base form is preferred. However, as depicted in the illustrative process below, it may be preferable, for example, to use the intermediate compound of formula (III) in the form of pharmaceutically acceptable salt such as the hydrochloride salt,

SCHEME 2

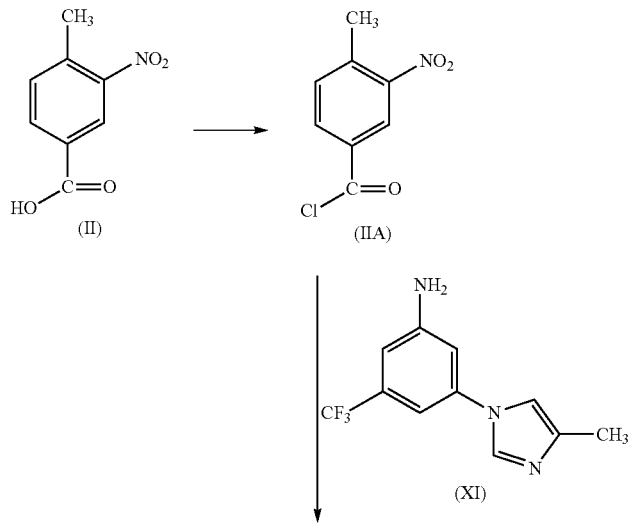

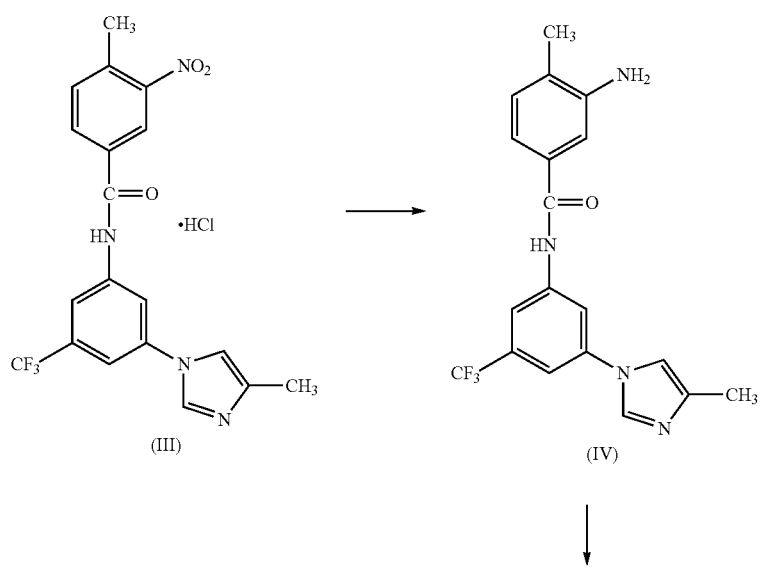

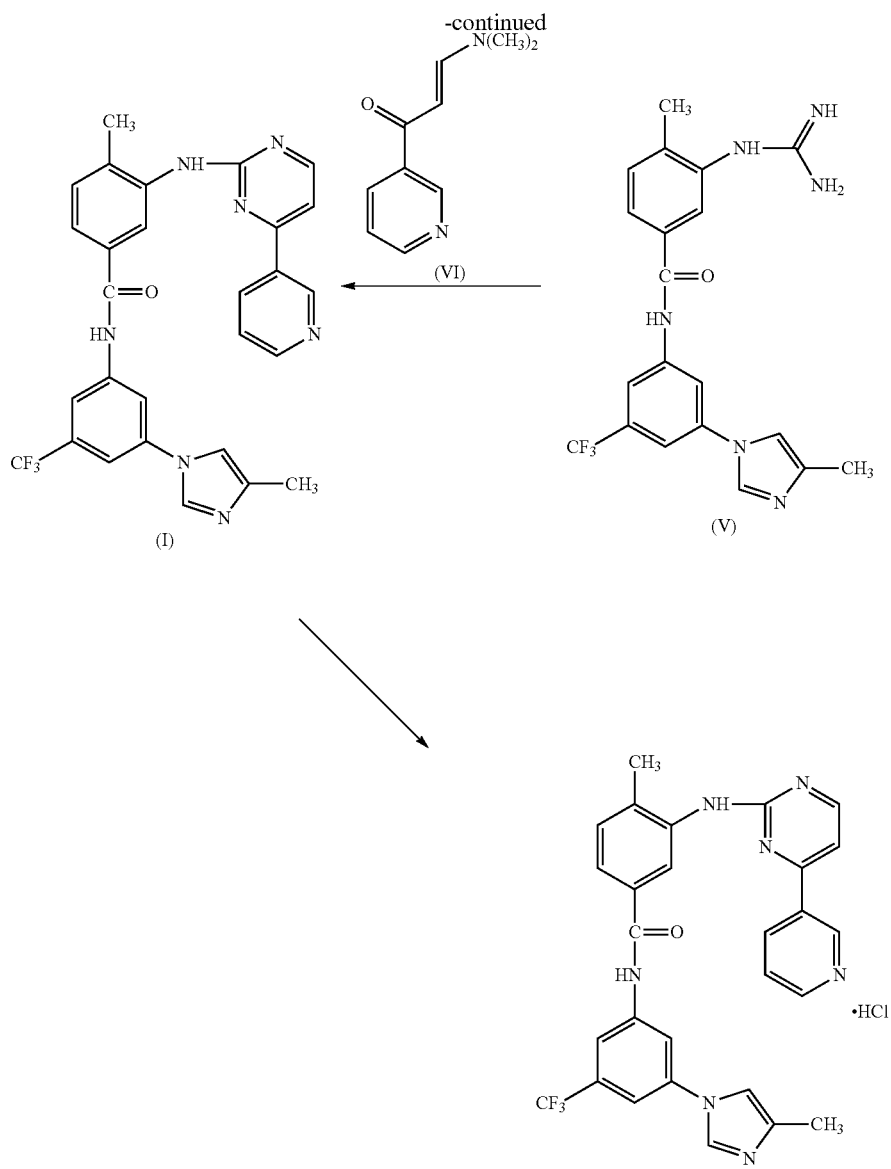

Nilotinib hydrochloride

Each step of the process of the present invention is discussed in further detail below.

The compound of formula (II) is 4-methyl-3-nitro benzoic acid. Preferably, the compound of formula (II) is chlorinated, to give the compound of formula (IIA), which is 4-methyl-3-nitro benzoyl chloride:

Chlorination can be achieved by conventional methods known to those skilled in the art. Preferably, chlorination is performed using SOCl$_2$ as the chlorinating agent.

The compound of formula (IIA) is then preferably reacted with a compound of formula (XI), to provide the compound of formula (III), which is 4-methyl-N-[3-(4-methyl-1H-imidazol-1-yl-5-(trifluoromethyl)phenyl]-3-nitro-benzamide:

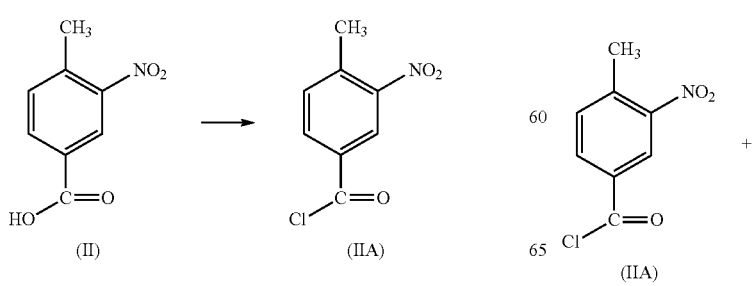

-continued

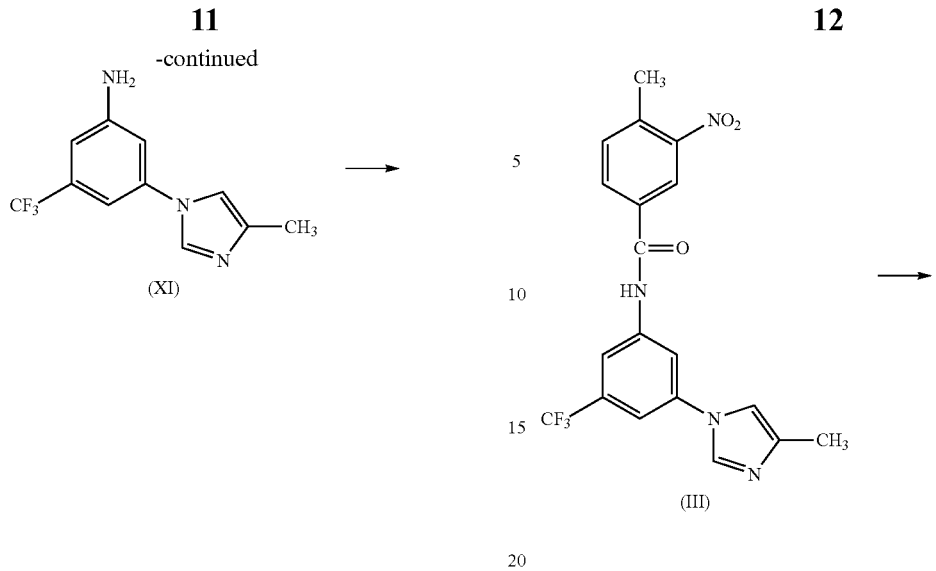

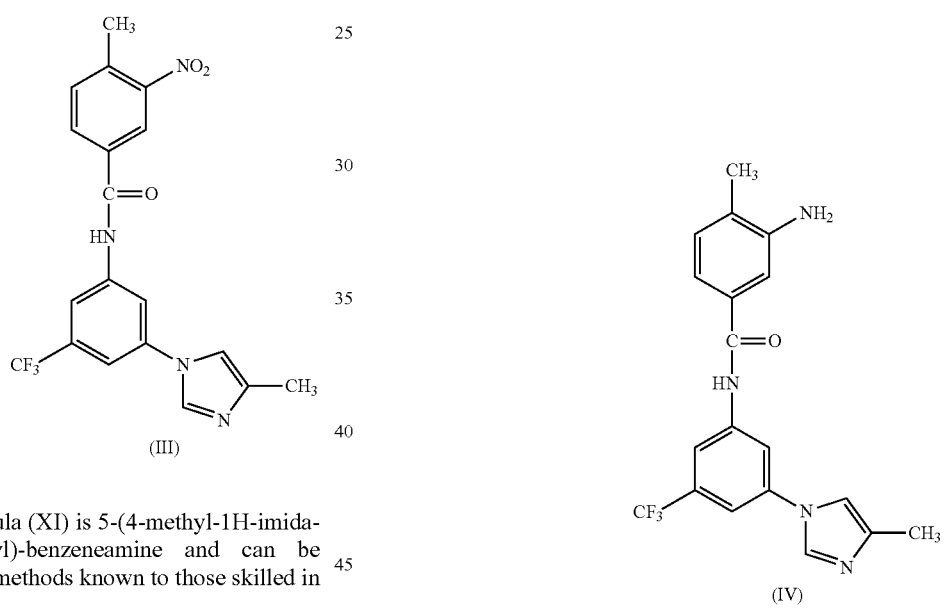

The compound of formula (XI) is 5-(4-methyl-1H-imidazol-1-yl)-3-(trifluoromethyl)-benzeneamine and can be obtained by conventional methods known to those skilled in the art.

The reaction of the compound of formula (IIA) with the compound of formula (XI) is typically carried out in the present of an alkali, preferably selected from sodium hydroxide or potassium hydroxide more preferably potassium hydroxide. The reaction of the compound of formula (IIA) with the compound of formula (XI) is typically carried out in a chlorinated hydrocarbon solvent, preferably methylene chloride or chloroform, more preferably chloroform. The reaction of the compound of formula (IIA) with the compound of formula (XI) is typically carried out at a temperature of 20-50° C., preferably 30-40° C.

The compound of formula (III) may be obtained, and then processed in subsequent steps of the process, in free base form or in pharmaceutically acceptable salt form, such as hydrochloride salt form.

The compound of formula (III) is then reduced, to give a compound of formula (IV), which is 4-methyl-N-[3-(4-methyl-1H-imidazol-1-yl-5-(trifluoromethyl)phenyl]-3-amino-benzamide.

The reduction of the compound of formula (III) can be conducted using using standard reduction conditions and reagents, which will be known to one skilled in the art.

For example, the reduction of the compound of formula (III) can be achieved using stannous chloride ($SnCl_2$). Typically, stannous chloride in a methanol solvent is used. A preferred reaction time is 2 to 3 hours.

Alternatively, the reduction of the compound of formula (III) can be achieved using by catalytic hydrogenation, typically using Raney nickel, preferably in a methanol medium.

The compound of formula (IV) is then converted into a compound of formula (I).

Typically this conversion is achieved by in a two-step transformation. Firstly, the compound of formula (IV) is reacted with cyanamide to obtain a compound of formula (V), which is 4-methyl-N-[3-(4-methyl-1H-imidazol-1-yl-5-(trifluoromethyl)phenyl]-3-guanidino-benzamide.

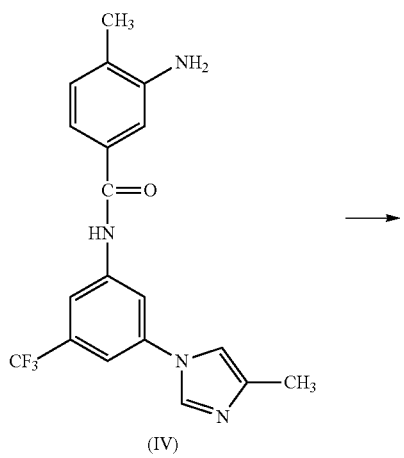

(IV)

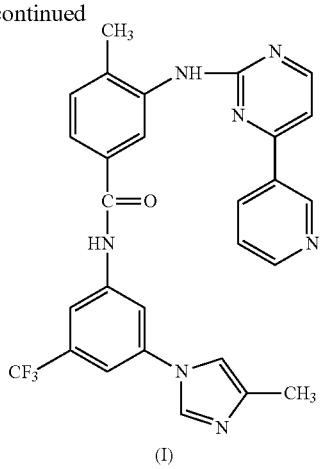

(I)

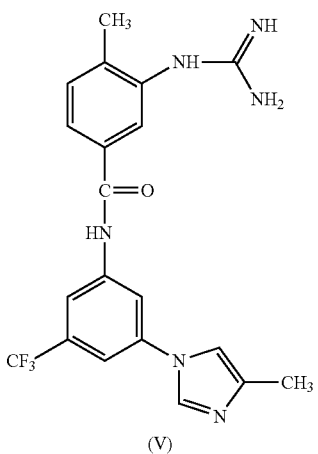

(V)

Typically, the cyanamide is dissolved in a $C_1$-$C_6$ alcohol, preferably n-butanol. Typically, the reaction temperature is 90-95° C., particularly when the solvent is n-butanol.

The compound of formula (V) is typically then reacted with a compound of formula (VI), to provide the compound of formula (I).

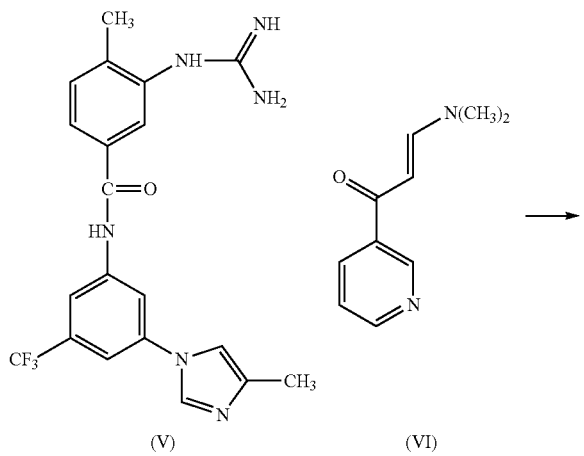

(V)      (VI)

The compound of formula (VI) is 3-dimethylamino-1-(3-pyridyl)-2-propen-1-one. Typically, this reaction occurs in the presence of a base. Reflux conditions and temperature are preferably used.

The compound of formula (I) may then be salified with a pharmaceutically acceptable acid, to form the corresponding pharmaceutically acceptable salt. For example, the compound of formula (I) can be converted into the hydrochloride salt by reaction with hydrochloric acid. Typically, concentrated hydrochloric acid in methanol and water medium is used to form the hydrochloride salt.

The present invention is also directed to the compound of formula (I) and to pharmaceutically acceptable salts thereof obtainable by the process of the invention. The present invention is in particular directed to the hydrochloride salt form of the compound of formula (I) obtainable by the process of the invention. The hydrochloride salt of the compound of formula (I) is preferably in the form of the dihydrate.

The moisture content of the compound of formula (I) or pharmaceutically acceptable salt thereof obtainable by the process of the invention is typically less than 10% by weight, preferably less than 7% by weight, more preferably less than 6% by weight, for example about 5% by weight.

The compound of formula (I) or pharmaceutically acceptable salt thereof prepared by the process of the present invention exists in a stable crystalline form. The crystalline form of the compound of formula (I) or pharmaceutically acceptable salt thereof obtainable by the process of the invention has an X-ray powder diffraction pattern with one or more peaks at 4.3, 8.7, 9.5, 11.3, 13.2, 14.4, 17.3, 18.6, 19.3, 20.8, 22.2 and 25.3 degrees 2θ (±0.1 degrees 2θ). Preferably two or more such peaks are observed, more preferably three or more, more preferably four or more, more preferably five or more. Most preferably all such peaks are observed.

It is particularly preferred that the crystalline form of the invention has an X-ray powder diffraction pattern with one or more peaks at 8.7, 17.3, 19.3, 22.2 and 25.3 degrees 2θ (±0.1 degrees 2θ). Preferably two or more such peaks are observed, more preferably three or more, more preferably four or more. Most preferably all such peaks are observed.

Typically, the peak at 8.7 degrees 2θ (±0.1 degrees 2θ) is most intense. Preferably, the peak at 8.7 degrees 2θ (±0.1 degrees 2θ) is at least twice as intense as the next most intense peak.

Preferably the crystalline form is the hydrochloride salt of the compound of formula (I), more preferably in the form of the dihydrate The crystalline form of the invention is thermally stable.

Typically, the X-ray powder diffraction pattern of a sample of the crystalline form of the invention which has been stored at 70° C. for 40 hours is identical, or substantially identical, to that of the crystalline form of the invention described above. Preferably, at least 90% by weight, more preferably 95%, more preferably 98%, of a sample of the crystalline form of the invention which has been stored at 70° C. for 40 hours retains the crystalline form of the invention described above.

Typically, the X-ray powder diffraction pattern of a sample of the crystalline form of the invention which has been stored at 40° C. and 75% relative humidity for 3 months is identical, or substantially identical, to that of the crystalline form of the invention described above. Preferably, at least 90% by weight, more preferably 95%, more preferably 98%, of a sample of the crystalline form of the invention which has been stored at 40° C. and 75% relative humidity for 3 months retains the crystalline form of the invention described above.

Typically, crystalline form of the invention is not hygroscopic. Typically, the moisture content of the crystalline form of the invention after storage for 60 days at 40° C. and 75% relative humidity is less than 10% by weight, more preferably less than 7% by weight, and most preferably less than 6.5% by weight.

The pharmaceutical composition of the invention comprises a compound of formula (I) or a pharmaceutically acceptable salt thereof in association with a pharmaceutically acceptable diluent or carrier. The purpose of a pharmaceutical composition is to facilitate administration of a compound to an organism. As used herein, a physiologically/pharmaceutically acceptable diluent or carrier refers to a carrier or diluent that does not cause significant irritation to an organism and does not abrogate the biological activity and properties of the administered compound. Suitable pharmaceutically acceptable carriers and diluents are well known to those skilled in the art.

The details of the invention are provided in the Example given below which are provided to illustrate the invention only and therefore they should not be construed to limit the scope of the invention.

EXAMPLE 1

(a) Preparation of 4-methyl-N-[3-(4-methyl-1H-imidazol-1-yl-5-(trifluoromethyl)phenyl]-3-nitro-benzamide hydrochloride of the formula (III)

To a suspension of 100 g (0.55 moles) of 3-amino-4-methylbenzoic acid of the formula (II) in chloroform (1 L) of thionyl chloride 131.5 g (1.10 moles) and dimethyl formamide (1 ml) were added. The reaction mass was heated to reflux temperature and maintained at the same temperature for 3 hours. Solvent chloroform was distilled off completely under vacuum and again 500 ml of chloroform was charged and distilled under vacuum to remove traces of thionyl chloride. The residual 3-amino-4-methylbenzoyl chloride of the formula (IIA) was taken to the following condensation step.

5-(4-methyl-1H-imidazol-1-yl)-3-(trifluoromethyl)-benzeneamine 110 g (0.45 moles) of formula (XI) was dissolved in 1 L of chloroform. 4-methyl-3-nitro benzoyl chloride of the formula (IIA) prepared above was added slowly to the reaction mass at 10-15° C. for 60 minutes. Reaction mass was raised to room temperature and maintained for 4 hours. Reaction mass was filtered, washed with chloroform and dried.

Yield: 161 g (87%)
Purity: 99% (by HPLC)
IR and NMR were consistent with the proposed structure.

(b) Preparation of 4-methyl-N-[3-(4-methyl-1H-imidazol-1-yl-5-(trifluoromethyl)phenyl]-3-amino-benzamide of the formula (IV)

To a chilled solution (10-15° C.) of stannous chloride 265.6 g (1.18 moles) in 400 ml methanol of 4-methyl-N-[3-(4-methyl-1H-imidazol-1-yl-5-(trifluoromethyl)phenyl]-3-nitro-benzamide hydrochloride 130 g (0.29 moles) of the formula (III) obtained from step (a) was added during 30 minutes. The reaction mass was maintained at 10-15° C. for one hour and heated to reflux temperature. The reaction mass was maintained at reflux temperature for 90 minutes and brought to room temperature. Purified water (600 ml) was charged to reaction mass at room temperature and maintained under stirring for 6-8 hours. Reaction mass was filtered, washed with 1N HCl and suck dried for 2 hours. Wet solid was charged into 2 L purified water, cooled to 10-15° C. and basified with 4% aqueous sodium hydroxide solution. Reaction mass was brought to room temperature and maintained at the same temperature for 2 hours, filtered and dried at 50-60° C. to yield compound of formula (IV).

Yield: 104 g (80%)
Purity: 99.4%(by HPLC)

Alternatively compound of formula (IV) can be prepared by the catalytic hydrogenation of compound of formula (III) with Raney nickel in methanol medium as follows:

Into hydrogenation kettle 50 g (0.123 moles) of 4-methyl-N-[3-(4-methyl-1H-imidazol-1-yl-5-(trifluoromethyl)phenyl]-3-nitro-benzamide hydrochloride of the formula (III) obtained from step (a) was charged into 250 ml methanol. Raney nickel (20 g) was charged into pressure reactor kettle and hydrogenated at a hydrogen gas pressure of 60 psi for 22 hours. After reaction completion reaction mass was filtered and washed with methanol. To the filtrate aqueous ammonia solution (45 ml) was charged and stirred for 30 minutes. Reaction mass was filtered, washed thoroughly with purified water and dried at 50-60° C. to yield compound of formula (IV)

Yield: 35 g (70%)
Purity: 99.0%(by HPLC)
IR: 210-212° C.
IR and NMR were consistent with the proposed structure.

(c) Preparation of 4-methyl-N-[3-(4-methyl-1H-imidazol-1-yl-5-(trifluoromethyl)phenyl]-3-guanidino-benzamide of the formula (V)

To a suspension of 80 g (0.213 moles) of 4-methyl-N-[3-(4-methyl-1H-imidazol-1-yl-5-(trifluoromethyl)phenyl]-3-amino-benzamide of the formula (IV) obtained from step (b) in 480 ml n-butanol 20.2 ml of concentrated hydrochloric acid was added. A solution of 18 g (0.427 moles) of cyanamide in 18 ml water was added and reaction mass was heated to 90-95° C. for 20 hours while maintaining pH at 2-3 with Conc. HCl (22 ml). Reaction mass was cooled to 10-15° C., filtered and washed with chilled n-butanol. Wet solid was charged into 1.5 L purified water and, basified with 40% aqueous sodium hydroxide solution. Reaction mass was maintained at room temperature for 2 hours, filtered, washed with water and dried at 60-65° C. to yield compound of formula (IV)
Yield: 86.3 g (97%)
IR and NMR were consistent with the proposed structure.

(d) Preparation of Nilotinib of the Formula (I)

A mixture of 65 g (0.156 moles) of 4-methyl-N-[3-(4-methyl-1H-imidazol-1-yl-5-(trifluoromethyl)phenyl]-3-guanidino-benzamide from step (c), 30.0 g (0.171 moles) of 3-dimethylamino-1-(3-pyridyl)-2-propen-1-one of the formula (VIII) in 650 ml n-butanol was heated at 110-115° C. for 9 hours. Reaction mass was brought to room temperature and the separated solid (70 g) was filtered off. Wet solid was leached with hot water (700 ml) and hot methanol (700 ml) successively. The wet product was dried at 60-65° C. under vacuum to yield compound of formula (I).
Yield: 52.1 g (63%)
MR: 235-236° C.
Purity: 99.0% (by HPLC)
IR and NMR were consistent with the proposed structure.

(e) Preparation of Nilotinib Hydrochloride

Into 1 L four neck flask a mixture of methanol (500 ml) and purified water (52.5 ml) was charged. Nilotinib (30 g) obtained from step (d) was charged into the flask. Concentrated hydrochloric acid (5.51 g) was dissolved in methanol (30 ml) and added to reaction mass for 15 minutes. Reaction mass was heated to reflux temperature and maintained at the same temperature for 15 minutes. Reaction mass was brought to 55-60° C. and clarified with activated carbon using mixture of methanol (30 ml) and purified water (3.25 ml) for washing. The clear solution was cooled to 0-5° C. and maintained at the same temperature for 3-4 hours. Thus formed Nilotinib hydrochloride was filtered, washed with chilled Isopropanol (30 ml) and dried in vacuum tray drier at 40-45° C.
This compound exhibits XRD pattern as depicted by FIG. 1. These data are set out in Table 1 below:
Yield: 26.3 g
Hydrochloride content: 6.26%
Moisture content by karl-fischer: 5.29% wt/wt

TABLE 1

| Peak position (degrees 2θ) | D-spacing (Å) | Relative intensity (%) |
|---|---|---|
| 8.6623 | 10.19987 | 100.00 |
| 9.5295 | 9.27347 | 2.82 |
| 11.3055 | 7.82037 | 7.67 |
| 13.1808 | 6.71163 | 1.59 |
| 14.3680 | 6.15963 | 1.99 |
| 17.3149 | 5.11735 | 15.92 |
| 18.6166 | 4.76364 | 6.40 |
| 19.2714 | 4.60201 | 13.61 |
| 20.8462 | 4.25779 | 1.41 |
| 22.1922 | 4.00248 | 3.30 |
| 25.2469 | 3.52471 | 22.25 |

EXAMPLE 2

Pure nilotinib hydrochloride (1 gm) prepared by the process described in Example 1(e) was taken in a boiling test tube and heated gradually in oil bath maintained at 60-70° C. The substance was examined by XRPD. The results are set out in Table 2.

TABLE 2

| Polymorph content before heating | Time of heating (hours) | Polymorph form detected after heating |
|---|---|---|
| Nilotinib hydrochloride having XRD characterization as in FIG. 1 | 10 | Nilotinib hydrochloride having XRD characterization as in FIG. 1. XRD pattern unchanged |
| Nilotinib hydrochloride having XRD characterization as in FIG. 1. | 20 | Nilotinib hydrochloride having XRD characterization as in FIG. 1. XRD pattern unchanged |
| Nilotinib hydrochloride having XRD characterization as in FIG. 1. | 30 | Nilotinib hydrochloride having XRD characterization as in FIG. 1. XRD pattern unchanged |
| Nilotinib hydrochloride having XRD characterization as in FIG. 1. | 40 | Nilotinib hydrochloride having XRD characterization as in FIG. 1. XRD pattern unchanged |

The above data suggest that Nilotinib hydrochloride prepared by Example 1(e) is not meta stable and is stable to heat even at 70° C./40 hours

EXAMPLE 3

The following Table 3 illustrates the formulation composition of Nilotinib hydrochloride prepared from step-(e) of Example 1

TABLE 3

| Components | mg/capsule |
|---|---|
| Nilotinib hydrochloride | 241.00 |
| MCC pH 102 | 107.00 |
| Calsium CMC | 30.00 |
| PG Starch | 15.00 |
| Sodium stearyl fumarate | 7.00 |

Procedure

Required quantities of Nilotinib hydrochloride and MCC pH 102 were accurately weighed and sifted through #40 meshes and mixed well. Calcium CMC and PG starch were sifted through #40 mesh and mixed to the above blend. This blend was lubricated with #40 mesh sodium stearyl fumarate and submitted for encapsulation.

This nilotinib hydrochloride formulation exhibits XRD pattern as depicted by FIG. 2. These data are set out in Table 4.

TABLE 4

| Peak position (degrees 2θ) | D-spacing (Å) | Relative intensity (%) |
|---|---|---|
| 4.2941 | 20.56110 | 1.51 |
| 8.6148 | 10.25590 | 100.00 |
| 9.4195 | 9.38148 | 3.76 |
| 11.2994 | 7.82460 | 7.10 |
| 13.2272 | 6.68818 | 1.47 |
| 14.4083 | 6.14249 | 4.59 |
| 17.2641 | 5.13230 | 18.47 |
| 19.2618 | 4.60428 | 14.32 |
| 22.2212 | 3.99733 | 15.90 |
| 25.2836 | 3.51967 | 18.34 |

EXAMPLE 4

Stability Under High Humidity Conditions

For illustration of non-hygroscopic nature of Nilotinib hydrochloride drug substance from Example 1 and capsules from Example 3 were kept in stability chambers maintained at 40° C./ 75% RH and the water contents of the samples were determined by karl-fischer method. The results are set out in Table 5 below.

TABLE 5

| Sample | Initial moisture Content (%) | Final moisture content after 60 days 40° C. at humidity of 75% |
|---|---|---|
| Nilotinib hydrochloride drug stance prepared from example-1 | 5.26 | 5.2% |
| Nilotinib hydrochloride capsules prepared from example-3 | 6.4 | 6.2% |

The above table shows that Nilotinib hydrochloride from Example 1 and nilotinib hydrochlode capsules from Example 3 are non-hygroscopic and have substantial stability even under humidity conditions.

EXAMPLE 5

The following Table 6 shows the stability of Nilotinib hydrochloride capsule formulation and drug substances under accelerated stress conditions (40±2° C., 75±5% RH, 6 months).

TABLE 6

| Polymorph characterizing of Nilotinib hydrochloride formulation (Example 3) Polymorph form detected by XRD | Polymorph of characterizing Nilotinib hydrochloride API (Example 1) Polymorph form detected by XRD | Duration of storage (months) at 40 ± 2° C./ 75 ± 5% RH |
|---|---|---|
| FIG. 2 | FIG. 1 | 0 Month |
| FIG. 2 | FIG. 1 | 1 Month |
| FIG. 2 | FIG. 1 | 2 Months |
| FIG. 2 | FIG. 1 | 3 Months |

The XRD spectra remained essentially the same and unchanged. The stability of Nilotinib hydrochloride API and formulation in accelerated high humidity stress conditions is thus established.

The invention claimed is:

1. A monohydrochloride salt of a compound of formula (I):

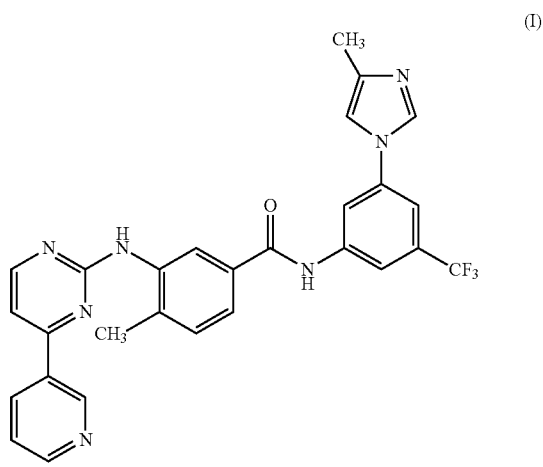 [SMILES: Cc1cn(-c2cc(NC(=O)c3ccc(C)c(Nc4nccc(-c5cccnc5)n4)c3)cc(C(F)(F)F)c2)cn1]

which is in the form of a dehydrate, and wherein the X-ray power diffraction pattern of a sample of the monohydrochloride salt which has been stored at 70° C. for 40 hours is substantially identical to that of the monohydrochloride salt prior to storage at 70° C. for 40 hours.

2. The monohydrochloride salt according to claim 1, which is crystalline and has an X-ray powder diffraction pattern with one or more peaks at 4.3, 8.7, 9.5, 11.3, 13.2, 14.4, 17.3, 18.6, 19.3, 20.8, 22.2 and 25.3 degrees 2θ(±0.1 degrees 2θ).

3. The monohydrochloride salt according to claim 1, wherein the X-ray powder diffraction pattern of a sample of the hydrochloride salt which has been stored at 40° C. and 75% relative humidity for 3 months is substantially identical to that of the monohydrochloride salt prior to storage at 40° C. and 75% relative humidity for 3 months.

4. A pharmaceutical composition comprising a monohydrochloride salt of compound as defined in claim 1 in association with a pharmaceutically acceptable diluent or carrier.

* * * * *